(12) United States Patent
Lee

(10) Patent No.: US 8,807,998 B2
(45) Date of Patent: Aug. 19, 2014

(54) ORTHODONTIC FIXING APPARATUS

(76) Inventor: Cheol-gyu Lee, Seoul (KR)

( * ) Notice: Subject to any disclaimer, the term of this patent is extended or adjusted under 35 U.S.C. 154(b) by 0 days.

(21) Appl. No.: 13/810,812

(22) PCT Filed: Jul. 20, 2011

(86) PCT No.: PCT/KR2011/005323
§ 371 (c)(1),
(2), (4) Date: Jan. 17, 2013

(87) PCT Pub. No.: WO2012/011728
PCT Pub. Date: Jan. 26, 2012

(65) Prior Publication Data
US 2013/0122446 A1 May 16, 2013

(30) Foreign Application Priority Data
Jul. 20, 2010 (KR) ...................... 20-2010-007579 U

(51) Int. Cl.
*A61C 7/00* (2006.01)
*A61C 7/12* (2006.01)
*A61C 8/00* (2006.01)

(52) U.S. Cl.
CPC .................. *A61C 7/12* (2013.01); *A61C 8/0096* (2013.01); *A61C 7/00* (2013.01); *Y10S 606/903* (2013.01)
USPC ................................ 433/18; 606/70; 606/903

(58) Field of Classification Search
USPC ............ 433/2, 3, 5–22, 24; 623/17.17–17.19; 606/70–71, 280–299, 902–906
See application file for complete search history.

(56) References Cited

U.S. PATENT DOCUMENTS 5,702,396 A    12/1997  Hoenig et al.
5,741,258 A     4/1998  Kalue et al.
(Continued)

FOREIGN PATENT DOCUMENTS

JP    2006-314419 A    11/2006
KR    10-2002-0017599 A    3/2002
(Continued)

OTHER PUBLICATIONS

Young Ho Kim et al. "Midpalatal Miniscrews for Orthodontic Anchorage: Factors Affecting Clinical Success" Am. J. Orthod. Dentofacial Orthop. 2010; vol. 137, No. 1, pp. 66-72.
(Continued)

Primary Examiner — Cris L Rodriguez
Assistant Examiner — Edward Moran
(74) Attorney, Agent, or Firm — Novick, Kim & Lee, PLLC; Jae Youn Kim

(57) ABSTRACT

An orthodontic fixing apparatus is provided, wherein the apparatus includes a linear fixing body, bisymmetrically defined, having a plurality of connection grooves in each left and right sides thereof, and a plurality of cylindrical fixing rings arranged on the upper and lower sides of the central portion of the fixing body with a connection member being placed between the upper and lower sides, wherein a screw is inserted, to thereby fix the fixing body to the palate. Each fixing ring may protrude by a width of 0.1 mm to 4 mm in a direction of contact with the palate to minimize the contact of the fixing ring or the fixing body with the palate. The fixing ring may include a taper having a diameter that gradually decreases from an inlet to an outlet along an insertion direction of the screw, wherein an internal thread is arranged in the fixing ring.

2 Claims, 3 Drawing Sheets

(56) References Cited

U.S. PATENT DOCUMENTS

| | | | |
|---|---|---|---|
| 5,853,291 A * | 12/1998 | DeVincenzo et al. | 433/176 |
| 6,821,278 B2 * | 11/2004 | Frigg et al. | 606/291 |
| 7,052,499 B2 * | 5/2006 | Steger et al. | 606/291 |
| 2003/0104335 A1 * | 6/2003 | Chung | 433/18 |
| 2007/0259306 A1 * | 11/2007 | Raines et al. | 433/18 |
| 2010/0004691 A1 * | 1/2010 | Amato et al. | 606/280 |

FOREIGN PATENT DOCUMENTS

| | | |
|---|---|---|
| KR | 20-0315723 Y1 | 6/2003 |
| KR | 10-2009-0077254 A | 7/2009 |
| KR | 20-2010-0004031 U | 4/2010 |
| KR | 10-2010-0138710 A | 12/2010 |
| KR | 10-1268646 B1 | 5/2013 |
| WO | 01/37751 A1 | 5/2001 |
| WO | 02/074181 A1 | 9/2002 |

OTHER PUBLICATIONS

Yasuhiro Itsuki et al. "A New Palatal Implant with Interchangeable Upper Units" Journal of Clinical Orthodontics, May 2009: vol. XLIII, No. 5, pp. 318-323.

Yoon-Ah Kook et al. "A Modified Palatal Anchorage Plate for Simple and Efficient Distalization" Journal of Clinical Orthodontics, Dec. 2010: vol. XLIV, No. 12, pp. 719-730.

W. K. Tsui et al. "Bone Anchor Systems for Orthodontic Application: A Systematic Review" Int. J. Oral Maxillofacial Surg. 2012; 41, pp. 1427-1438.

Heinrich Wehrbein. "Bone Quality in the Midpalate for Temporary Anchorage Device" Clin. Oral Impl. Res. 20, 2009; pp. 45-49.

Sungmin Kang et al. "Bone Thickness of the Palate for Orthodontic Mini-Implant Anchorage in Adults" Am. J. Orthod. Dentofacial Orthop. Apr. 2007; vol. 131, No. 4, pp. S74-S81.

Kyu-Rhim Chung et al. "Class II Malocclusion Treated by Combining a Lingual Retractor and a Palatal Plate" Am. J. Orthod. Dentofacial Orthop. Jan. 2008; vol. 133, No. 1, pp. 112-123.

S. H. Kyung et al. "Distalization of Maxillary Molars with a Midpalatal Miniscrew" Journal of Clinical Orthodontics, Jan. 2003: vol. XXXVII, No. 1, pp. 22-26.

Seung-Hyun Kyung et al. "Distalization of the Entire Maxillary Arch in an Adult" Am. J. Orthod. Dentofacial Orthop. Apr. 2009; vol. 135, No. 4, pp. S125-132.

Richard M. Hesby et al. "Transverse Skeletal and Dentoalveolar Changes During Growth" Am. J. Orthod. Dentofacial Orthop. Dec. 2006: vol. 130, No. 6, pp. 721-731.

Yoon-Ah Kook, et al. "Design Improvements in the Modified C-Palatal Plate for Molar Distalization" JCO, Inc., vol. XLVII No. 4, Apr. 2013, pp. 241-248.

* cited by examiner

ORTHODONTIC FIXING APPARATUS

TECHNICAL FIELD

The present invention relates to an orthodontic fixing apparatus, wherein the fixing apparatus is placed to a palate for use as an anchorage during orthodontic treatment, particularly aimed at a more effective orthodontic treatment through easier insertion of a screw while minimizing contact area with the palate.

BACKGROUND ART

In general, a fixing apparatus fixed to a palate during orthodontic treatment is used to move anterior teeth protruding to the front into the back of the mouth or into a specific direction.

In prior arts, a molar is used as such anchorage. More particularly, a predetermined bracket is attached to the molar and the teeth to be moved, and then, for example, a variety of archwire or an elastic material such as a spring or a rubber band, i.e., elastic chain, is connected to the bracket to ensure that the molar is fixed in place.

However, when the molar is used as an anchorage, the teeth to be moved is pulled by the molar acting as an anchorage (as an action) and simultaneously the molar is pulled from the teeth to be moved (as a reaction). Thus there is a problem of the movement of the molar, acting as an anchorage, to a certain extent.

A separate fixing apparatus, i.e., extra oral appliance, can be placed to prevent the movement of the anchorage. However, this can cause discomfort to a patient and thus there is a problem that treatment cannot be properly given without the patient's cooperation.

Therefore, recently, a method of placing a fixing apparatus to a bone in the palate, by inserting a screw, has been widely used. Namely, it comprises inserting the screw to the bone in the palate and attaching a predetermined bracket to the desired teeth to be moved, then connecting the brackets and the screw to an elastic material such as a spring or an elastic chain, or to a wire fixed to the bracket, and pulling with some force to move the teeth (usually the anterior teeth).

When the screw is inserted to the fixing apparatus and used as mentioned above, not only is movement of the molar prevented but the procedure is simplified and an effective orthodontic treatment can be achieved in a short amount of time. However, since there is no measure to hold the screw fixed in the fixing apparatus, it is difficult to place the fixing apparatus at an exact location due to movement of the screw to the left and right when implanting the screw to the palate through the fixing apparatus. Also, there is a problem of an inflammation or damage in the palate due to a large contact area between the palate and the fixing apparatus having a flat structure.

DETAILED DESCRIPTION OF THE INVENTION

Technical Problem

The present invention provides an orthodontic fixing apparatus that aims to solve the aforementioned problem by minimizing contact between the palate and the fixing apparatus as well as simplifying insertion of the screw to enable an efficient orthodontic treatment.

The technical objective of the present invention is not limited to the aforementioned technical problem, and technical problems not mentioned above can be clearly understood by a person skilled in the art by the disclosure below.

Technical Solution

In order to achieve the above identified objective, the orthodontic fixing apparatus of the present invention comprises a linear fixing body, bisymmetrically defined, having a plurality of connection grooves in each left and right sides thereof, and a plurality of cylindrical fixing ring, arranged on upper and lower sides of a central portion of the fixing body with a connection member being placed between the upper and lower sides, wherein a screw is inserted into the ring to fix the fixing body to a palate.

In one embodiment, the fixing ring protrudes by a width of 0.1 mm to 4 mm in a direction of contact with the palate to minimize contact of the fixing body or the fixing ring in contact with the palate.

In another embodiment, the fixing ring comprises a taper having a diameter that gradually decreases from an inlet to an outlet along an insertion direction of the screw, wherein an internal thread is arranged in the fixing ring.

Advantageous Effects

According to the above mentioned orthodontic fixing apparatus, the screw is firmly supported when inserted into the palate, and thus, the fixing apparatus can act as a solid anchorage. Also, as the placing of the fixing apparatus is simple, it is convenient to use the fixing apparatus, and inflammation or damage of the palate can be prevented since contact between the palate and the fixing apparatus is minimized when the fixing apparatus is placed into the palate.

EMBODIMENTS

Figure 1:
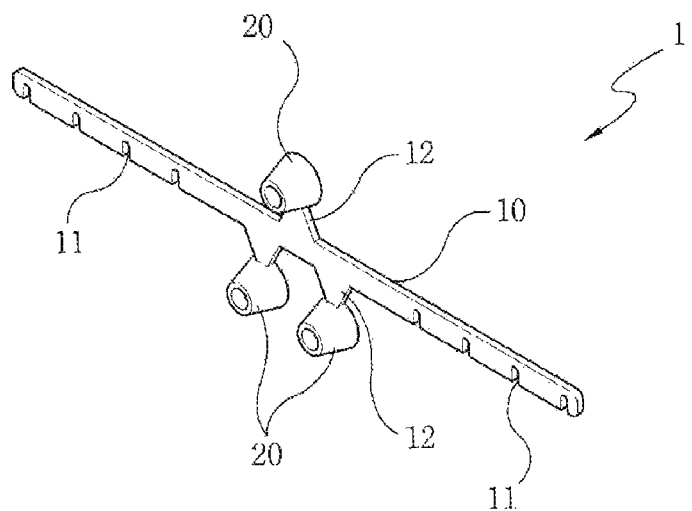
FIG. 1 is a perspective view of an orthodontic fixing apparatus according to the present invention.

The present invention is described hereinafter in detail using exemplary embodiments with reference to the accompanying figures to enable a person skilled in the art to easily carry out the invention. However, the present invention can be of various structures and is not limited to the embodiments described hereafter.

The technical terms used herein are only for reference to specific embodiments and is not intended to limit the scope of the present invention. A singular form of a term used herein comprises a plural form of a term unless the phrases clearly define contrarily. Throughout this specification the term "comprise" specifies a specific feature, region, integer, step, action, element and/or component, but does not exclude the presence or addition of a different specific feature, area, integer, step, action, element, component and/or group.

Although not defined separately, all the terminology, including technical and scientific terms, used in the present invention have identical meaning to what is apparent to a person skilled in art to which the present invention pertains. The terms that are normally used, which are defined in the dictionary, are additionally understood to have corresponding definitions to what is disclosed here and the related technical art. Unless defined, it is not understood as preferred or formal.

The embodiment of the present invention described with reference to perspective views represents the preferred embodiment in detail. As a result, various modifications, for example, modifications of manufacturing method and/or specification are expected. Thus, the embodiment is not limited to the specific structure shown by the drawing and includes, for example, modification of the structure by a manufacturing method. For instance, the areas defined as flat can generally have rough/rough and nonlinear features. Also, areas indicated as sharp can be round. Therefore, the indicated areas in the drawings are only an approximation, and are not intended to show the exact structure of said areas or to limit the scope of the present invention.

Figure 2:
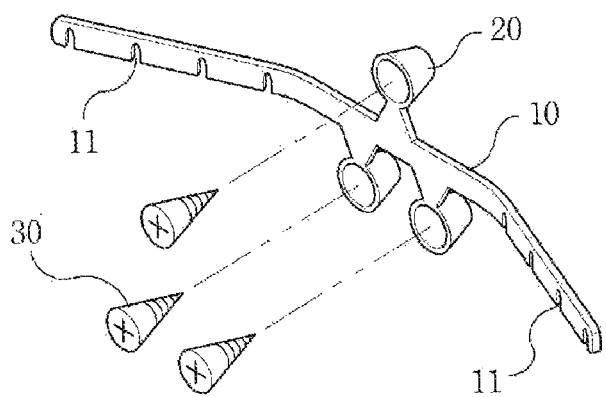
FIG. 2 is an assembling perspective view showing a screw being inserted to an orthodontic fixing apparatus according to the present invention.

In explaining the structure of the orthodontic fixing apparatus according to the present invention with reference to FIGS. 1 and 2, said orthodontic fixing apparatus (1) mainly comprises a fixing body (10) and a fixing ring (20).

In other words, the fixing body (10) of said orthodontic fixing apparatus (1) is a linear member, bisymmetrically defined, having a plurality of connection grooves (11) placed at predetermined intervals at left and right sides of the fixing body, a plurality of said fixing ring (20) are arranged on upper and lower sides of a central portion of said fixing body (10) with a connection member (12) being placed between the upper and lower sides, and said fixing ring (20) is cylindrical, such that a screw (30) is inserted into said fixing ring (20) to fix said fixing body (10) to a palate.

Here, said fixing body (10) is comprised of a material able to bend, and one end of an orthodontic ligature such as a wire, an elastic chain or a spring is removably connected to the connection grooves (11) formed on the left and right of the fixing body.

Further, said fixing ring (20) protrudes by a width of 0.1 mm to 4 mm in a direction of contact with the palate, to minimize contact of said fixing body (10) or said fixing ring (20) in contact with the palate.

The protruding width of said fixing ring (20) is variously manufactured to have a range of 0.1 mm to 4 mm, and a fixing apparatus (1) with an appropriate measurement can be selected for use, as necessary.

In other words, a screw (30) is inserted into said fixing ring (20) to fix the fixing body (10) to the palate. When said orthodontic fixing apparatus (1) is fixed to the palate by said fixing ring (20) protruding to a certain width, it is to separate said fixing body (10) and the palate by a predetermined distance.

Therefore, said orthodontic fixing apparatus (1) first bends both sides of said fixing body (10) at a certain angle to fix it to the palate, and at this state said fixing screw (30) is inserted into said fixing ring (20) to fix the fixing ring (20) to the palate.

Figure 3:
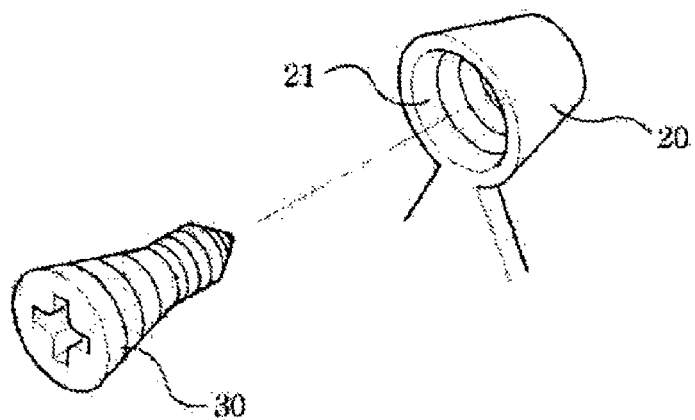
FIG. 3 is an enlarged assembling perspective view of a fixing ring of an orthodontic fixing apparatus according to the present invention.

Meanwhile, in explaining the structure of a fixing ring (20) of said orthodontic fixing apparatus (1) with reference to FIG. 3, said fixing ring (20) comprises a taper having a diameter that decreases from an inlet to an outlet along an insertion direction of a screw (30), wherein an internal thread (21) is arranged therein, and said screw (30) inserted into said fixing ring (20) is firmly fixed.

Therefore, it is possible to firmly support said screw (30) that is inserted through said fixing ring (20) shaped as a taper form, and said screw (30) is inserted into said fixing ring (20) through an internal thread (21) arranged inside the fixing ring, while keeping a straight vertical state to fix the screw to the palate.

Figure 4:
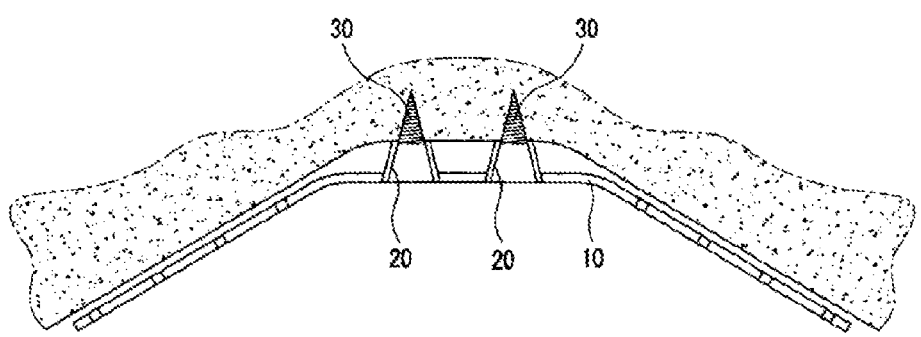
FIG. 4 is a cross sectional view of an orthodontic fixing apparatus placed in a palate according to the present invention.

Here, in explaining said orthodontic fixing apparatus (1) as installed with reference to FIG. 4, said fixing body (10) is made of a material that is able to bend according to a shape of the palate when said fixing body is fixed to the palate, and accordingly said fixing body (10) is placed in the palate with both sides bent, and because said fixing ring (20) comes in contact with the palate at a protruded state, a central portion of said fixing body (10) and the palate are separated to prevent inflammation or damage in the palate.

That is, the contact area between the orthodontic fixing apparatus (1) and the palate is minimized by said protruding fixing ring (20).

Figure 5:
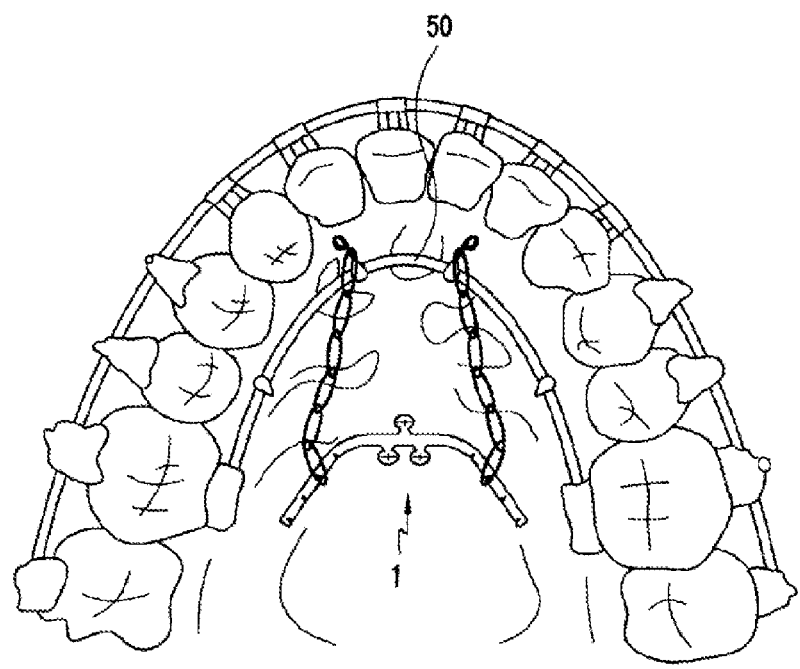
FIG. 5 is an assembled view of an orthodontic ligature connected to an orthodontic fixing apparatus according to the present invention.

Then, in explaining said orthodontic fixing apparatus (1) connected to a correction ligature with reference to FIG. 5, a wire among correction ligature parts as a rule is connected to the connection grooves (11) formed in said orthodontic fixing apparatus (1), and said wire can be placed by various methods depending on the correction treatment objective.

Thus, one end of said wire is fixed to said connection grooves (11), and the other end of said wire is connected to the teeth to be corrected and the bracket and wire (50) etc. placed on the teeth, to put into effect the pulling and bearing capacities on the teeth to be corrected, by defining orthodontic fixing apparatus (1) as the anchorage.

Therefore, it is possible to promote an efficient orthodontic treatment by improving structure of the orthodontic fixing apparatus (1) as stated above.

The present invention is not limited in scope by the preferred embodiments described herein. The present invention may be variously modified and carried out within the range of claims, detailed description of the invention and the accompanying drawings, which also belong to the scope of the present invention.

The invention claimed is:

1. An orthodontic fixing apparatus comprising;
   an elongated linear fixing body having a central portion, a left side portion and a right side portion, wherein the left and right side portions each have a plurality of connection grooves located at predetermined distances and formed in said left and right side portions and which are open to a lower side of said left and right side portions;
   a single upper connection member fixed to an upper side of the central portion of the linear fixing body and two lower connection members fixed to a lower side of the central portion of the linear fixing body;
   a single upper conical fixing ring attached to the upper connection member and two lower conical fixing rings attached to the lower connection members;
   wherein a screw is inserted into each of the upper and lower conical fixing rings along a screw insertion direction adapted to fix the linear fixing body to a palate;
   wherein each of the upper and lower conical fixing rings comprises constantly tapered inner and outer surfaces which gradually decrease in diameter from an upper inlet end to a lower outlet end along the screw insertion direction;
   wherein the upper inlet ends of each conical fixing ring are flush with the linear fixing body and the upper and lower conical fixing rings protrude outwards from the body in the screw insertion direction towards the lower outlet end and towards the palate to minimize contact of the fixing body with the palate;

wherein an internal thread is arranged in each of the upper and lower conical fixing rings; and wherein the orthodontic fixing apparatus is symmetric about a vertical axis located at the midpoint of and perpendicular to a longitudinal axis of the device.

2. The orthodontic fixing apparatus in accordance with claim 1, wherein each of the at least one upper and lower conical fixing rings protrudes by a height of 0.1 mm to 4 mm toward the palate from the linear fixing body.

\* \* \* \* \*